United States Patent [19]

Finizio

[11] 4,267,185
[45] May 12, 1981

[54] ANTIDEPRESSANT PYRROLYLPIPERIDINES, THEIR PHARMACEUTICAL COMPOSITIONS AND METHOD OF USE

[75] Inventor: Michael Finizio, Wilmington, Del.

[73] Assignee: E. I. Du Pont de Nemours and Company, Wilmington, Del.

[21] Appl. No.: 138,706

[22] Filed: Apr. 9, 1980

[51] Int. Cl.³ .................. C07D 401/02; A61K 31/455
[52] U.S. Cl. .................... 424/267; 424/263; 546/208; 546/281
[58] Field of Search ................ 546/208, 281; 424/263, 424/267

[56] References Cited

U.S. PATENT DOCUMENTS

| 2,890,220 | 6/1959 | Omietanski | 546/281 |
| 3,230,226 | 1/1966 | Bernasek | 456/281 |
| 3,429,885 | 2/1969 | Archibald | 456/281 |
| 3,523,950 | 8/1970 | Helsley | 546/281 |

OTHER PUBLICATION

Chem. Abs., Vol. 79 (1973) Item 115, 448a, abstracting Nakanishi et al. (Yoshitomi Pharmaceutical Industries, L.T.D.)

Primary Examiner—Henry R. Jiles
Assistant Examiner—Robert T. Bond

[57] ABSTRACT

The pyrrolylpiperidines, 1-methyl-4-(1-methylpyrrol-2-yl)-4-piperidinol, 1,2,3,6-tetrahydro-1-methyl-4-(1-methylpyrrol-2-yl)pyridine, and pharmaceutically acceptable salts thereof are useful as antidepressant agents.

7 Claims, No Drawings

ANTIDEPRESSANT PYRROLYLPIPERIDINES, THEIR PHARMACEUTICAL COMPOSITIONS AND METHOD OF USE

BACKGROUND OF THE INVENTION

1. Field of Invention

This invention relates to pyrrolylpiperidines, processes for their preparation and uses as antidepressants.

2. Prior Art

Mental illnesses include psychoses and neuroses. The symptoms requiring treatment include depression, anxiety, agitation and hallucinations. Drugs used particularly for treatment of both reactive and endogenous depressions include monoamine oxidase (MAO) inhibitors such as iproniazide, tranylcypromine, nialamide, phenelzine and pargyline and the non-MAO inhibiting tricyclic aromatic dibenzazepines such as imipramine and dibenzocycloheptadienes such as amitriptyline.

All of these drugs have side effects that limit their usefulness. The MAO inhibitors may cause tremors, insomnia, hyperhydrosis, agitation, hypermaniac behavior, confusion, hallucinations, convulsions, orthostatic hypertension and death. They frequently cause dizziness, vertigo, headache, inhibition of ejaculation, difficulty in urination, weakness, fatigue, dry mouth, constipation and blurred vision. Imipramine may cause blurred vision, dryness of mouth, constipation, urinary retention, orthostatic hypotension, respiration depression, myocardial infarction and congestive heart failure. Similar difficulties are experienced with amitriptyline.

There is a genuine need for psychotherapeutic agents which are effective and have fewer side effects than the drugs in use today. There is also a need for drugs which have different modes of action than the presently used ones since none is completely effective. The compounds of the present invention satisfy these criteria.

Japanese published Appln. No. 73/56687 to Yoshitomi Pharmaceutical Industries, Inc. discloses antidiabetic and antiinflammatory agents including compounds of the formula:

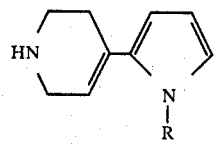

where R = H or alkyl. The compounds are prepared by dehydrating the corresponding piperidinols.

SUMMARY OF THE INVENTION

According to the present invention there is provided a compound selected from the group consisting of:
(a) 1-methyl-4-(1-methylpyrrol-2-yl)-4-piperidinol,
(b) 1,2,3,6-tetrahydro-1-methyl-4-(1-methylpyrrol-2-yl)pyridine, and
(c) a pharmaceutically acceptable salt of (a) or (b).

There is also provided a pharmaceutical composition containing an effective antidepressant amount of at least one of the above-mentioned compounds, and a method of using the compounds to treat depression in a mammal.

Further provided is a process for preparing a compound as described above comprising:

(a) contacting n-butyllithium with N-methylpyrrole dissolved in an inert solvent,
(b) contacting the resulting lithium salt with 1-methyl-4-piperidone at a temperature in the range of about 0° C. to about 25° C., and
(c) recovering the resulting 1-methyl-4-(1-methylpyrrol-2-yl)-4-piperidinol, or forming a pharmaceutically acceptable salt thereof, or dehydrating it by contacting it with a dehydrating agent to form 1,2,3,6-tetrahydro-1-methyl-4-(1-methylpyrrol-2-yl)-pyridine.

DETAILED DESCRIPTION OF THE INVENTION

The compounds of the invention have the following structural formulas:

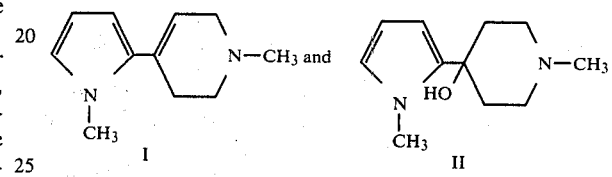

The compound of formula I is 1,2,3,6-tetrahydro-1-methyl-4-(1-methylpyrrol-2-yl)pyridine and the compound of formula II is 1-methyl-4-(1-methylpyrrol-2-yl)-4-piperidinol.

The compound of formula II is prepared by reacting n-butyllithium with a slight stoichiometric excess of N-methylpyrrole dissolved in an inert solvent, preferably diethyl ether. Since this reaction proceeds readily, no particular reaction conditions are critical. However, it is preferred that the reaction be carried out by stirring at reflux for 4–20 hrs.

The resulting lithium salt is then reacted with 1-methyl-4-piperidone at a temperature in the range of about 0° C. to about 25° C. Here again, other reaction conditions are not critical; but, it is preferred that this reaction step be carried out by dropwise addition of 1-methyl-4-piperidone at about 0° C.

The above reactions are shown by the following reaction sequence:

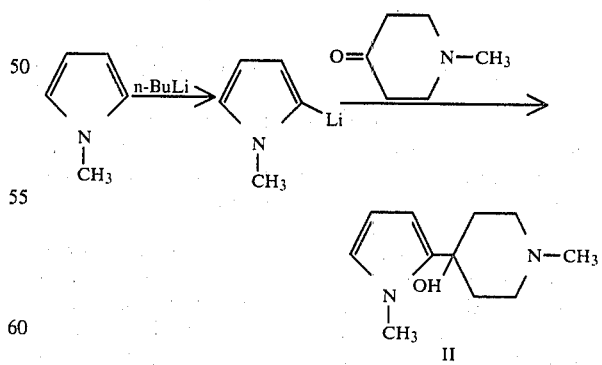

The compound of formula I is prepared by dehydration of II with a suitable mild dehydrating agent such as an alumina, a silica, or a silicate. As used herein, the term "dehydrating agent" means a mild chemical compound which removes water from the organic compounds without attacking the rest of the molecule.

Strong, known dehydrating agents such as sulfuric acid and phosphorus pentoxide are not suitable.

The dehydration reaction of formula II compound is carried out by heating II in toluene at reflux in the presence of the mild dehydrating agent for 1–5 hrs.

The compounds of formulas I and II can also be used in the pharmaceutical compositions and methods of the invention in the form of a salt thereof to provide the correct amount of the base. Salts are formed with any of the pharmaceutically acceptable acids well known to those skilled in the art of medicinal chemistry or pharmaceuticals. Examples of such acceptable acids are hydrochloric, sulfuric, phosphoric, nitric, hydrobromic, oxalic, maleic, succinic, benzoic, lactic and pamoic. The hydrochloric acid salts are preferred.

EXAMPLE 1

1-Methyl-4-(1-methylpyrrol-2-yl)-4-piperidinol

A 1.6 M solution of n-butyllithium in hexane (175 ml) was added dropwise at room temperature to a solution of 24.2 g of N-methylpyrrole in 250 ml of diethyl ether contained in a reaction flask (under a nitrogen blanket). After addition was completed, the resulting mixture was heated at reflux with stirring for 16 hours, then cooled to 0° C. 34 Grams of 1-methyl-4-piperidone was added dropwise from a dropping funnel with the temperature maintained at 0° C. during the addition by cooling the reaction flask with dry ice-acetone bath. The reaction mixture was stirred at room temperature for 3 hours, and then quenched in ice water to yield 26 g of the title compound in a crystalline form; recrystallization from heptane gave white prisms, m.p. 123°–123.5°.

EXAMPLE 2

1,2,3,6-Tetrahydro-1-methyl-4-(1-methylpyrrol-2-yl)pyridine, hydrochloride salt

A mixture of 3 g of 1-methyl-4-(1-methylpyrrol-2-yl)-4-piperidinol, 3 g Florisil ®*, and 50 ml of toluene was heated at reflux for 5 hours, cooled to room temperature, decanted, evaporated to leave a heavy oil which was dissolved in 20 ml of diethyl ether. Gaseous HCl was bubbled through the solution to yield the title compound in crystalline form. Yield: 2.2 g, mp 222°–230° C.

*Florisil ® is a synthetic absorbent manufactured by Floridin Co. which is a magnesium silicate.

Dosage Forms

The antidepressant agents of this invention can be administered to treat depression of the reactive and endogenous types by any means that produce contact of the active agent with the agent's site of action in the body of a mammal. They can be administered by any conventional means available for use in conjunction with pharmaceuticals; either as individual therapeutic agents or in a combination of therapeutic agents. For example, administration can be parenterally, i.e., subcutaneously, intravenously, intramuscularly or intraperitoneally. Alternatively or concurrently, administration can be by the oral route. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.1 to 8.0. milligrams per kilogram of body weight. Ordinarily 0.25 to 4.0 and preferably 0.5 to 2.0 milligrams per kilogram per day given in divided doses 2 to 4 times a day or in sustained release form is effective to obtain desired results.

Dosage forms (compositions) suitable for internal administration contain from about 1.0 milligram to about 500 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage form, such as elixirs, syrups, and suspensions; it can also be administered parenterally, in sterile liquid dosage forms.

Gelatin capsules contain the active ingredient and powdered carriers, such as lactose, sucrose, manitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coating for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition, parenteral solutions can contain preservatives, such as benzalkonium chloride, methyl- or propyl- paraben and chlorobutanol.

Suitable pharmaceutical carriers are described in *Remington's Pharmaceutical Sciences*, E. W. Martin, a standard reference text in this field.

Useful pharmaceutical dosage forms for administration of the compounds of this invention can be illustrated as follows:

Capsules

A large number of unit capsules are prepared by filling standard two-piece hard gelatin capsules each with 25 milligrams of powdered active ingredient, 200 milligrams of lactose, 24 milligrams of talc, and 6 milligrams magnesium stearate.

A mixture of active ingredient in soybean oil is prepared and injected by means of a positive displacement pump into gelatin to form soft gelatin capsules containing 25 milligrams of the active ingredient. The capsules are washed in petroleum ether and dried.

Tablets

A large number of tablets are prepared by conventional procedures so that the dosage unit is 25 milligrams of active ingredient, 0.2 milligrams of colloidal silicon dioxide, 5 milligrams of magnesium stearate, 275 milligrams of microcrystalline cellulose, 11 milligrams of cornstarch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is made isotonic with sodium chloride and sterilized by filtration.

Suspension

An aqueous suspension is prepared for oral administration so that each 5 milliliters contain 25 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

Antidepressant Utility

The antidepressant activity of the compounds of the invention is evidenced by tests conducted in female white mice in which prevention of tetrabenazine-induced sedation and depression is demonstrated. This mouse test is predictive of human antidepressant response (Everett, "The Dopa Response Potentiation Test and Its Use in Screening for Antidepressant Drugs," pp. 164 in "Antidepressant Drugs" (Proceedings of the First International Symposium), S. Garattini and M. N. G. Dukes, eds., 1967).

EXAMPLE A

Groups of 10 Carworth $CF_1S$ female mice, 18–21 g each, were fasted 1.5 hours and were intubated with antagonist compounds at oral doses of 0, 0.33, 1, 3, 9, 27, and 81 mg/kg in 0.20 ml of 1% Methocel-1.25% Tween 80. The mice were challenged 30 minutes later with tetrabenazine (as the methanesulfonate), 32 mg/kg intraperitoneally (dissolved in 0.20 ml 0.05 M KCl at pH 2.0). One hour after antagonist (30 minutes after tetrabenazine), the mice were examined for signs of exploratory activity and ptosis (eyelid closure). Normal exploratory activity (relief from sedation) was recorded when a mouse lifted by the tail from a group of 10 in a testing box and placed on a stainless testing box lid (12.5"×8" with 0.33" mesh) either turned its head horizontally 30° in both directions or moved to the edge of the screen within 10 seconds after being placed on the screen. Relief from ptosis was recorded when exactly two seconds after placing the mouse facing the observer, lid closure was less than 50% in both eyes. Table 1 gives the results.

TABLE 1
ANTAGONISM OF TETRABENAZINE-INDUCED DEPRESSION IN MICE ORALLY AT 1 HOUR POST-DRUG

| COMPOUND | ED50 (mg/kg) for PREVENTION OF | |
|---|---|---|
| | Exploratory Loss | Ptosis |
| Example 2 | 1.4 | 0.8 |
| Example 1 | 1.8 | 1.1 |
| Amitriptyline | 3.5 | 1.4 |

What is claimed is:

1. A compound selected from the group consisting of:
   (a) 1-methyl-4-(1-methylpyrrol-2-yl)-4-piperidinol,
   (b) 1,2,3,6-tetrahydro-1-methyl-4-(1-methylpyrrol-2-yl)pyridine, and
   (c) a pharmaceutically acceptable salt of (a) or (b).

2. A pharmaceutical composition consisting essentially of a pharmaceutically acceptable carrier and an effective antidepressant amount of a compound of claim 1.

3. The pharmaceutical composition of claim 2 wherein the compound is 1-methyl-4-(1-methylpyrrol-2-yl)-4-piperidinol or a pharmaceutically acceptable salt thereof.

4. The pharmaceutical composition of claim 2 wherein the compound is 1,2,3,6-tetrahydro-1-methyl-4-(1-methylpyrrol-2-yl)pyridine or a pharmaceutically acceptable salt thereof.

5. A method of treating depression in a mammal comprising administering to the mammal an effective amount of a compound of claim 1.

6. The method of claim 5 wherein the compound is 1-methyl-4-(1-methylpyrrol-2-yl)-2-piperidinol or a pharmaceutically acceptable salt thereof.

7. The method of claim 5 wherein the compound is 1,2,3,6-tetrahydro-1-methyl-4-(1-methylpyrrol-2-yl)-pyridine or a pharmaceutically acceptable salt thereof.

* * * * *